United States Patent [19]

Kingston et al.

[11] Patent Number: 5,232,930
[45] Date of Patent: Aug. 3, 1993

[54] 2-HETEROARYL-SUBSTITUTED BENZODIOXOIC HAVING 5-LIPOXYGENASE INHIBITORY ACTIVITY

[75] Inventors: John F. Kingston, Tytherington; David Waterson, Bollington, both of England

[73] Assignees: Imperial Chemical Industries PLC, London, England; ICI Pharma, Cergy, France

[21] Appl. No.: 818,680

[22] Filed: Jan. 9, 1992

[30] Foreign Application Priority Data

Jan. 15, 1991 [EP] European Pat. Off. ......... 91400078.1

[51] Int. Cl.$^5$ ............... A61K 31/34; A61K 31/47; A61K 31/40; C07D 217/00; C07D 407/04; C07D 317/46; C07D 263/54; C07D 215/14
[52] U.S. Cl. ................ 514/314; 514/249; 514/227.8; 514/230.5; 514/297; 514/307; 514/393; 514/394; 514/422; 544/48; 544/52; 544/105; 544/283; 544/353; 546/117; 546/118; 546/144; 546/157; 546/158; 548/159; 548/235; 548/466; 548/305.1; 548/361.1
[58] Field of Search ............. 544/105, 52, 48, 283, 544/353; 546/157, 158, 117, 118, 144; 549/13, 59, 435, 443, 445; 514/249, 227.8, 230.5, 297, 314, 307, 393, 394, 422; 548/159, 235, 327, 466

[56] References Cited

U.S. PATENT DOCUMENTS

| 3,400,130 | 9/1968 | Shroff | 546/157 X |
| 3,661,917 | 5/1972 | Kaiser et al. | 546/172 |

(List continued on next page.)

FOREIGN PATENT DOCUMENTS

| 0110405 | 6/1984 | European Pat. Off. | 546/172 |
| 0181568 | 5/1986 | European Pat. Off. | 546/172 |
| 0190722 | 8/1986 | European Pat. Off. | 546/152 |
| 0200101 | 12/1986 | European Pat. Off. | 544/317 |
| 0271287 | 6/1988 | European Pat. Off. | 546/152 |
| 0349062 | 6/1989 | European Pat. Off. | 517/277 |
| 1056022 | 5/1959 | Fed. Rep. of Germany | 549/435 |

OTHER PUBLICATIONS

Bird et al, Chemical Abstracts, vol. 115, #29299h (1991).
Crawley et al I, Chemical Abstracts, vol. 114, #228757k (1991).
Crawley et al II, Chemical Abstracts, vol. 115, #114375z (1991).
Edwards et al I, Chemical Abstracts, vol. 114, #228732y (1991).
Edwards et al II, Chemical Abstracts, vol. 115, #183096w (1991).

*Primary Examiner*—Floyd D. Higel

[57] ABSTRACT

The invention concerns a benzodioxole derivative of the formula I

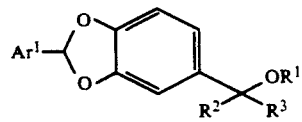

wherein $Ar^1$ is an optionally substituted 9- or 10-membered bicyclic heterocyclic moiety containing one or two nitrogen heteroatoms and optionally containing a further heteroatom selected from nitrogen, oxygen and sulphur;

$R^1$ is (1-6C)alkyl, (3-6C)alkenyl or (3-6C)alkynyl; and $R^2$ and $R^3$ together form a group of the formula $-A^1-X-A^2-$ which, together with the carbon atom to which $A^1$ and $A^2$ are attached, defines a ring having 5 to 7 ring atoms, wherein each of $A^1$ and $A^2$ is (1-3C)alkylene and X is oxy, thio, sulphinyl or sulphonyl, and which ring may bear one or two substituents;

or a pharmaceutically-acceptable salt thereof;

which compounds are inhibitors of 5-lipoxygenase and are useful in the treatment of inflammatory or allergic disease.

7 Claims, No Drawings

U.S. PATENT DOCUMENTS

| Patent No. | Date | Inventor | Class |
|---|---|---|---|
| 3,743,737 | 7/1973 | Kaiser et al. | 546/172 |
| 4,258,185 | 3/1981 | Nakao et al. | 436/158 X |
| 4,567,184 | 1/1986 | Musser et al. | 514/277 |
| 4,625,034 | 11/1986 | Neiss et al. | 546/152 |
| 4,631,287 | 12/1986 | Chakraborty et al. | 514/307 |
| 4,725,619 | 2/1988 | Chakraborty et al. | 514/442 |
| 4,728,668 | 3/1988 | Chakraborty et al. | 514/464 |
| 4,770,507 | 9/1988 | Campbell et al. | 546/157 X |
| 4,794,188 | 12/1988 | Musser et al. | 546/152 |
| 4,818,755 | 4/1989 | Kuhza et al. | 546/157 X |
| 4,839,369 | 6/1989 | Youssefyeh et al. | 514/314 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |
| 5,091,533 | 2/1992 | Belanger et al. | 546/157 X |
| 5,098,930 | 3/1992 | Edwards | 514/459 |
| 5,098,932 | 3/1992 | Hamon | 514/462 |
| 5,105,020 | 4/1992 | Girodeau | 568/633 |
| 5,126,365 | 6/1992 | Bird et al. | 514/451 |
| 5,132,328 | 7/1992 | Girodeau | 514/716 |

2-HETEROARYL-SUBSTITUTED BENZODIOXOIC HAVING 5-LIPOXYGENASE INHIBITORY ACTIVITY

This invention concerns novel benzodioxole derivatives and more particularly novel benzodioxole derivatives which are inhibitors of the enzyme 5-lipoxygenase (hereinafter referred to as 5-LO). The invention also concerns processes for the manufacture of said derivatives and novel pharmaceutical compositions containing them. Also included in the invention is the use of said derivatives in the treatment of various inflammatory and/or allergic diseases in which the direct or indirect products of 5-LO catalysed oxidation of arachidonic acid are involved, and the production of new medicaments for such use.

As stated above the benzodioxole derivatives described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

It is disclosed in European Patent Applications Nos. 0375404 and 0385662 that certain heterocyclic derivatives possess inhibitory properties against 5-LO. Copending European Patent Application Nos. 0409413 and 0420511 (published Jan. 23, 1991 and Apr. 3, 1991 respectively i.e. after the priority date of the present invention) are also concerned with heterocyclic derivatives which possess inhibitory properties against 5-LO.

Copending European Patent Application No. 0410661 (published Jan. 30, 1991 i.e. after the priority date of the present application) describes certain benzo-1,3-dioxole derivatives bearing in the 2-position an aryl group such as phenyl or naphthyl. The compounds therein possess inhibitory properties against 5-LO.

We have now discovered that certain benzodioxole derivatives are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a benzodioxole derivative of the formula I (set out hereinafter) wherein $Ar^1$ is a 9- or 10-membered bicyclic heterocyclic moiety containing one or two nitrogen heteroatoms and optionally containing a further heteroatom selected from nitrogen, oxygen and sulphur, and $Ar^1$ may optionally bear up to three substituents selected from amino, halogeno, hydroxy, cyano, oxo, thioxo, (1-4C)alkyl, (1-4C)alkoxy, (1-4C)alkylthio, (1-4C)alkylsulphinyl, (1-4C)alkylsulphonyl, (1-4C)alkylamino, di-[(1-4C)alkyl]amino, (1-4C)alkoxycarbonyl, (2-4C)alkanoyl and fluoro-(1-4C)alkyl;

wherein the benzodioxole ring may optionally bear one or two substituents selected from halogeno, hydroxy, (1-4C)alkyl, (1-4C)alkoxy and fluoro-(1-4C)alkyl;

wherein $R^1$ is (1-6C)alkyl, (3-6C)alkenyl or (3-6C)alkynyl; and wherein $R^2$ and $R^3$ together form a group of the formula —$A^1$—X—$A^2$— which, together with the carbon atom to which $A^1$ and $A^2$ are attached, defines a ring having 5 to 7 ring atoms, wherein $A^1$ and $A^2$, which may be the same or different, each is (1-3C)alkylene and X is oxy, thio, sulphinyl or sulphonyl, and which ring may bear one or two substituents, which may be the same or different, selected from hydroxy, (1-4C)alkyl and (1-4C)alkoxy;

or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of formula I defined above may exist in optically active or racemic forms by virtue of one or more asymmetric carbon atoms, the invention includes in its definition of active ingredient any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techiques referred to hereinafter.

Suitable values for the generic terms referred to above include those set out below.

A suitable value for $Ar^1$ when it is a 9- or 10-membered bicyclic heterocyclic moiety containing one or two nitrogen heteroatoms and optionally containing a further heteroatom selected from nitrogen, oxygen and sulphur is, for example, a 9- or 10-membered benzofused heterocyclic moiety such as indolyl, isoindolyl, benzimidazolyl, 1H-indazolyl, benzoxazolyl, benzothiazolyl, quinolyl, isoquinolyl, cinnolinyl, quinazolinyl, quinoxalinyl, 4H-1,4-benzoxazinyl or 4H-1,4-benzothiazinyl, or a hydrogenated derivative thereof such as indolinyl, 2,3-dihydrobenzimidazolyl, 2,3-dihydrobenzoxazolyl, 2,3-dihydrobenzothiazolyl, 1,2-dihydroquinolyl, 1,2,3,4-tetrahydroquinolyl, 1,2-dihydroisoquinolyl, 2,3-dihydro-4H-1,4-benzoxazinyl or 2,3-dihydro-4H-1,4-benzothiazinyl; or, for example, a 9- or 10-membered pyrido-fused heterocyclic moiety such as 1H-pyrrolo[2,3-b]pyridyl, imidazo[4,5-b]pyridyl, 1,7-naphthyridinyl, 1,8-naphthyridinyl, pyrido[2,3-d]pyrimidine, pyrido[2,3-b]pyrazine, 4H-pyrido[3,2-b][1,4]oxazine and 4H-pyrido[3,2-b][1,4]thiazine, or a hydrogenated derivative thereof.

The heterocyclic moiety may be attached through any available position including from either of the two rings of the bicyclic heterocyclic moiety and including through an available nitrogen atom. The heterocyclic moiety may bear a suitable substituent such as, for example, a (1-4C)alkyl substituent on an available nitrogen atom.

Additional substituents on the benzodioxole ring, if present, are located on the benzo-ring portion thereof.

A suitable value for a halogeno substituent which may be present on $Ar^1$ or on the benzodioxole ring is, for example, fluoro, chloro, bromo or iodo.

A suitable value for a (1-4C)alkyl substituent which may be present on $Ar^1$ or on the benzodioxole ring is, for example, methyl, ethyl, propyl, isopropyl, butyl, isobutyl, sec-butyl or tert-butyl.

A suitable value for a (1-4C)alkoxy substituent which may be present on $Ar^1$ or on the benzodioxole ring is, for example, methoxy, ethoxy, propoxy, isopropoxy or butoxy.

Suitable values for substituents which may be present on $Ar^1$ include, for example:

| | |
|---|---|
| for (1-4 C) alkylthio: | methylthio, ethylthio, propylthio, isopropylthio and butylthio; |
| for (1-4 C) alkylsulphinyl: | methylsulphinyl, ethylsulphinyl, propylsulphinyl, isopropylsulphinyl and butylsulphinyl; |
| for (1-4 C) alkylsulphonyl: | methylsulphonyl, ethylsulphonyl, propylsulphonyl, isopropylsulphonyl and butylsulphonyl; |
| for (1-4 C) alkylamino: | methylamino, ethylamino, propylamino and butylamino; |
| for di-[(1-4 C) alkyl]amino: | dimethylamino, diethylamino and dipropylamino; |
| for (1-4 C) alkoxycarbonyl: | methoxycarbonyl, ethoxycarbonyl and tert-butoxycarbonyl. |

A suitable value for a fluoro-(1-4C)alkyl substituent which may be present on $Ar^1$ or on the benzodioxole ring is, for example, fluoromethyl, difluoromethyl, trifluoromethyl, 2-fluoroethyl, 2,2,2-trifluoroethyl and pentafluoroethyl.

A suitable value for a (2-4C)alkanoyl substituent which may be present on $Ar^1$ is, for example, acetyl, propionyl, butyryl or isobutyryl.

A suitable value for $R^1$ when it is (1-6C)alkyl is, for example, methyl, ethyl, propyl, butyl, pentyl or hexyl; when it is (3-6C)alkenyl is, for example, allyl, 2-butenyl or 3-butenyl; and when it is (3-6C)alkynyl is, for example, 2-propynyl or 2-butynyl.

When $R^2$ and $R^3$ together form a group of the formula —$A^1$—X—$A^2$— which, together with the carbon atom to which $A^1$ and $A^2$ are attached, defines a ring having 5 to 7 ring atoms then a suitable value for $A^1$ or $A^2$, which may be the same or different, when each is (1-3C)alkylene is, for example, methylene, ethylene or trimethylene.

Suitable values for the one or two substituents which may be present on said 5- to 7-membered ring include for example:

| | |
|---|---|
| for (1-4 C) alkyl: | methyl, ethyl, propyl, isopropyl and butyl; |
| for (1-4 C) alkoxy: | methoxy, ethoxy, propoxy, isopropoxy and butoxy. |

A suitable pharmaceutically-acceptable salt of a benzodioxole derivative of the invention is, for examole, an acid-addition salt of a benzodioxole derivative of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a benzodioxole derivative of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, benzodioxole derivatives of the formula I wherein:

(a) $Ar^1$ is indolyl, indolinyl, benzimidazolyl, 2,3-dihydrobenzimidazolyl, benzoxazolyl, 2,3-dihydrobenzoxazolyl, benzothiazolyl, 2,3-dihydrobenzothiazolyl, quinolyl, 1,2-dihydroquinolyl, isoquinolyl, 1,2-dihydroisoquinolyl, quinoxalinyl, 2,3-dihydro-4H-1,4-benzoxazinyl or 2,3-dihydro-4H-1,4-benzothiazinyl, which may optionally bear one oxo or thioxo substituent and up to two further substituents selected from any of those substituents on $Ar^1$ defined hereinbefore other than oxo or thioxo; and the benzodioxole ring, $R^1$, $R^2$ and $R^3$ have any of the meanings defined hereinbefore;

(b) $Ar^1$ is 2-indolyl, 3-indolyl, 5-indolyl, 6-indolyl, 2-benzimidazolyl, 5-benzimidazolyl, 6-benzimidazolyl, 2-benzoxazolyl, 5-benzoxazolyl, 6-benzoxazolyl, 2-benzothiazolyl, 5-benzothiazolyl, 6-benzothiazolyl, 2-quinolyl, 3-quinolyl, 6-quinolyl, 7-quinolyl, 3-isoquinolyl, 6-isoquinolyl, 7-isoquinolyl, 2-quinoxalinyl, 6-quinoxalinyl, 4H-1,4-benzoxazin-6-yl or 4H-1,4-benzothiazin-6-yl, which may optionally bear one oxo or thioxo substituent and up to two further substituents selected from any of those substituents on $Ar^1$ defined hereinbefore other than oxo or thioxo; and the benzodioxole ring, $R^1$, $R^2$ and $R^3$ have any of the meanings defined hereinbefore;

(c) $Ar^1$ is 2-oxoindolinyl, 2-oxo-2,3-dihydrobenzimidazolyl, 2-oxo-2,3-dihydrobenzoxazolyl, 2-oxo-2,3-dihydrobenzothiazolyl, 2-oxo-1,2-dihydroquinolinyl, 3-oxo-2,3-dihydro-4H-1,4-benzoxazinyl or 3-oxo-2,3-dihydro-4H-1,4-benzothiazinyl, or the corresponding thioxo derivatives thereof, which may optionally bear up to two substituents selected from any of those substituents on $Ar^1$ defined hereinbefore other than oxo or thioxo; and the benzodioxole ring, $R^1$, $R^2$ and $R^3$ have any of the meanings defined hereinbefore;

(d) $Ar^1$ is 2-oxoindolin-5-yl, 2-oxo-2,3-dihydrobenzimidazol-5-yl, 2-oxo-2,3-dihydrobenzoxazol-5-yl, 2-oxo-2,3-dihydrobenzothiazol-5-yl, 2-oxo-1,2-dihydroquinolin-3-yl, 2-oxo-1,2-dihydroquinolin-6-yl, 2-oxo-1,2-dihydroquinolin-7-yl, 3-oxo-2,3-dihydro-4H-

1,4-benzoxazin-7-yl or 3-oxo-2,3-dihydro-4H-1,4-benzothiazol-7-yl, which may optionally bear up to two substituents selected from any of those substituents on $Ar^1$ defined hereinbefore other than oxo or thioxo; and the benzodioxole ring, $R^1$, $R^2$ and $R^3$ have any of the meanings defined hereinbefore;

(e) $Ar^1$ is quinolyl, 1,2-dihydroquinolyl, 1,2,3,4-tetrahydroquinolyl or 2,3-dihydro-4H-1,4-benzoxazinyl which may optionally bear one oxo or thioxo substituent and up to two further substituents selected from any of those substituents on $Ar^1$ defined hereinbefore other than oxo or thioxo; and the benzodioxole ring, $R^1$, $R^2$ and $R^3$ have any of the meanings defined hereinbefore;

(f) $Ar^1$ is 2-oxo-1,2-dihydroquinolinyl, 2-thioxo-1,2-dihydroquinolinyl, 2-oxo-1,2,3,4-tetrahydroquinolinyl, 2-thioxo-1,2,3,4-tetrahydroquinolinyl or 3-oxo-2,3-dihydro-4H-1,4-benzoxazinyl which may optionally bear up to two substituents selected from any of those substituents on $Ar^1$ defined hereinbefore other than oxo or thioxo; and the benzodioxole ring, $R^1$, $R^2$ and $R^3$ have any of the meanings defined hereinbefore;

(g) the benzodioxole ring may optionally bear one substituent selected from fluoro, chloro, hydroxy, methyl, methoxy and trifluoromethyl; and $R^1$, $R^2$ and $R^3$ have any of the meanings defined hereinbefore;

(h) $R^1$ is methyl, ethyl, allyl or 2-propynyl; and $Ar^1$, the benzodioxole ring, $R^2$ and $R^3$ have any of the meanings defined hereinbefore;

(i) $R^1$ is methyl, ethyl or allyl; and $Ar^1$, the benzodioxole ring, $R^2$ and $R^3$ have any of the meanings defined hereinbefore;

(j) $R^2$ and $R^3$ together form a group of the formula $-A^1-X-A^2-$ which, together with the carbon atom to which $A^1$ and $A^2$ are attached, defines a ring having 5 to 7 ring atoms, wherein $A^1$ and $A^2$, which may be the same or different, each is methylene, ethylene or trimethylene and X is oxy, thio, sulphinyl or sulphonyl, and which ring may bear a substituent selected from hydroxy, methyl, methoxy and ethoxy; and $Ar^1$, the benzodioxole ring and $R^1$ have any of the meanings defined hereinbefore; or (k) $R^2$ and $R^3$ together form a group of the formula $-A^1-X-A^2-$ which, together with the carbon atom to which $A^1$ and $^2$ are attached, defines a ring having 5 or 6 ring atoms, wherein $A^1$ is ethylene, $A^2$ is methylene or ethylene and X is oxy, and which ring may bear one or two substituents, which may be the same or different, selected from methyl, ethyl and propyl; and $Ar^1$, the benzodioxole ring and $R^1$ have any of the meanings defined hereinbefore;

or a pharmaceutically-acceptable salt thereof.

A preferred compound of the invention comprises a benzodioxole derivative of the formula I wherein $Ar^1$ is 1-methyl-2-oxo-1,2-dihydroquinolin-6-yl, 1-ethyl-2-oxo-1,2-dihydroquinolin-6-yl, 1-methyl-2-oxo-1,2,3,4-tetrahydroquinolin-6-yl, 1-ethyl-2-oxo-1,2,3,4-tetrahydroquinolin-6-yl or the corresponding 2-thioxo derivatives, or $Ar^1$ is 4-methyl-3-oxo-2,3-dihydro-4H-1,4-benzoxazin-7-yl; the benzodioxole ring bears no additional substituents; $R^1$ is methyl, ethyl or allyl; and $R^2$ an $R^3$ together from a group of the formula $-A^1-X-A^2-$ which, together with the carbon atom to which $A^1$ and $A^2$ are attached, defines a ring having 5 or 6 ring atoms, wherein $A^1$ is ethylene, $A^2$ is methylene or ethylene and X is oxy, and which ring may bear a substituent selected from methyl and ethyl; or a pharmaceutically-acceptable salt thereof.

An especially preferred compound of the invention comprises a benzodioxole derivative of the formula I wherein $Ar^1$ is 1-methyl-2-oxo-1,2-dihydroquinolin-6-yl, 1-methyl-2-thioxo-1,2-dihydroquinolin-6-yl, 1-methyl-2-oxo-1,2,3,4-tetrahydroquinolin-6-yl, 1-methyl-2-thioxo-1,2,3,4-tetrahydroquinolin-6-yl or 4-methyl-3-oxo-2,3-dihydro-4H-1,4-benzoxazin-7-yl; the benzodioxole ring bears no additional substituents; $R^1$ is methyl; and $R^2$ and $R^3$ together form a group of the formula $-A^1-X-A^2-$ which, together with the carbon atom to which $A^1$ and $A^2$ are attached, defines a ring having 6 ring atoms, wherein $A^1$ is ethylene, $A^2$ is ethylene and X is oxy, and which ring may bear a methyl substituent alpha to X; or a pharmaceutically-acceptable salt thereof.

A specific especially preferred compound of the invention is the following benzodioxole derivative of the formula I, or a pharmaceutically-acceptable salt thereof:

5-(4-methoxytetrahydropyran-4-yl)-2-(1-methyl-2-oxo-1,2-dihydroquinolin-6-yl)benzo-1,3-dioxole.

A compound of the invention comprising a benzodioxole derivative of the formula I as defined hereinbefore, or a pharmaceutically-acceptable salt thereof, may be prepared by any process known to be applicable to the preparation of structurally-related compounds. Such processes are provided as a further feature of the invention. For the purpose of illustration only non-limiting examples of the application of such processes are provided hereinafter. Within the description of these processes $Ar^1$, the benzodioxole ring, $R^1$, $R^2$ and $R^3$ have any of the meanings defined hereinbefore. Alternatively, where appropriate, conventional protecting groups are utilised on functional groups which would otherwise interfere with the required process. Examples of such conventional protecting groups are provided hereinafter. Thereafter any such protecting group is removed by conventional means.

(a) The alkylation, preferably in the presence of a suitable base, of a compound of the formula II with a compound of the formula $R^1$-Z wherein Z is a suitable displaceable group.

A suitable displaceable group Z is, for example, a halogeno or sulphonyloxy group, for example a fluoro, chloro, bromo, iodo, methanesulphonyloxy or toluene-p-sulphonyloxy group.

A suitable base for the alkylation reaction is, for example, an alkali or alkaline earth metal carbonate, (1-4C)alkoxide, hydroxide or hydride, for example sodium carbonate, potassium carbonate, sodium ethoxide, potassium butoxide, sodium hydroxide, potassium hydroxide, sodium hydride or potassium hydride. The alkylation reaction is preferably performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near ambient temperature.

(b) The oxidative rearrangement of a compound of the formula III in the presence of a suitable oxidising agent.

A suitable oxidising agent is, for example, any agent known in the art for such an oxidative rearrangement, for example sodium or potassium metaperiodate. In general the reaction is carried out in a suitable solvent or diluent such as a polar solvent, for example aqueous methanol or aqueous ethanol and at a temperature in the range, for example, 15° to 35° C., conveniently at or near ambient temperature.

(c) The alkylation, preferably in the presence of a suitable base, of a compound of the formula IV with a compound of the formula $Ar^1$—$CH(Z)_2$ wherein Z is a suitable displaceable group as defined hereinbefore.

A suitable base for the alkylation reaction is, for example, one of the bases defined hereinbefore within the disclosure of process variant (a). Alternatively a suitable base is, for example, an organic base such as, for example, triethylamine, N-methylmorpholine, piperidine or pyridine. In general the reaction is carried out in a suitable solvent or diluent such as, for example, an excess of one of the above-mentioned organic bases, or N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

(d) The cyclisation, in the presence of a suitable acid, of a compound of the formula IV with an aldehyde of the formula $Ar^1$—CHO.

A suitable acid for the cyclisation reaction is, for example, an inorganic acid such as hydrochloric, sulphuric or phosphoric acid, or, for example, an organic acid such as p-toluenesulphonic acid or trifluoroacetic acid. The cyclisation reaction is conveniently performed in a suitable inert solvent or diluent, for example toluene or 1,2-dimethoxyethane. The cyclisation is effected at a temperature in the range, for example, 20° to 150° C., conveniently at or near the boiling point of the diluent or solvent and under conditions wherein the water produced as the cyclisation proceeds is separated, for example by use of a Dean and Stark apparatus.

(e) For the production of those compounds of the formula I wherein $Ar^1$ bears an alkylsulphinyl or alkylsulphonyl substituent, or wherein $R^2$ and $R^3$ together form a group of the formula —$A^1$—X—$A^2$— and X is a sulphinyl or sulphonyl group; the oxidation of a compound of the formula I wherein $Ar^1$ bears an alkylthio substituent, or wherein $R^2$ and $R^3$ together form a group of the formula —$A^1$—X—$A^2$— and X is a thio group.

A suitable oxidising agent is, for example, any agent known in the art for the oxidation of thio to sulphinyl and/or sulphonyl, for example, hydrogen peroxide, a peracid (such as m-chloroperbenzoic or peroxyacetic acid), an alkali metal peroxysulphate (such as potassium peroxymonosulphate), chromium trioxide or gaseous oxygen in the presence of platinum. The oxidation is generally carried out under as mild conditions as possinle and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(f) For the production of those compounds of the formula I wherein $Ar^1$ bears an alkyl or substituted alkyl substituent on an available nitrogen atom, the alkylation of a compound of the formula I wherein $Ar^1$ bears a hydrogen atom on said available nitrogen atom.

A suitable alkylating agent is, for example, any agent known in the art for the alkylation of an available nitrogen atom, for example an alkyl or substituted alkyl halide, for example a (1-4C)alkyl chloride, bromide or iodide or a substituted (1-4C)alkyl chloride, bromide or iodide, in the presence of a suitable base. A suitable base for the alkylation reaction is, for example, one of the bases defined hereinbefore within the disclosures of process variant (a). The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

(g) For the production of those compounds of the formula I wherein $Ar^1$ bears one or more thioxo substituents, the reaction of a benzodioxole derivative of the formula I wherein $Ar^1$ bears one or more oxo substituents with a thiation reagent such that each oxo substituent is converted into a thioxo substituent; provided that, when there is an amino, alkylamino or hydroxy group in $Ar^1$, $R^2$ or $R^3$ any such group may be protected by a conventional protecting group or alternatively any such group need not be protected, whereafter any undesired protecting group in $Ar^1$, $R^2$ and $R^3$ is removed by conventional means.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

(h) For the production of those compounds of the formula I wherein $Ar^1$ is a 9- or 10-membered bicyclic heterocyclic moiety containing one or two nitrogen heteroatoms and optionally containing a further heteroatom selected from nitrogen, oxygen and sulphur, and wherein $Ar^1$ bears an oxo substituent adjacent to a nitrogen heteroatom and said nitrogen heteroatom bears an alkyl or substituted alkyl substituent, the reaction of the appropriate unsubstituted heterocyclic moiety with an alkylating agent and the oxidation of the heterocyclic salt so obtained; provided that, when there is an amino, alkylamino or hydroxy group in $Ar^1$, $R^2$ or $R^3$ any such group may be protected by a conventional protecting group or alternatively any such group need not be protected, whereafter any undesired protecting group in $Ar^1$, $R^2$ and $R^3$ is removed by conventional means.

A suitable alkylating agent is, for example, any agent known in the art for the alkylation of an available nitrogen atom, for example an alkyl or substituted alkyl halide, for example a (1-4C)alkyl chloride, bromide or iodide or a substituted (1-4C)alkyl chloride, bromide or iodide, in the presence of a suitable base. A suitable base for the alkylation reaction is, for example, one of the bases defined hereinbefore within the disclosure of process variant (a). The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

The oxidation of the heterocyclic salt so obtained may be performed by standard procedures of organic chemistry or utilising methods, for example, by way of suitable oxidoreductase enzymes such as the quinine-oxidising enzyme of rabbit liver. Conveniently the oxidation may be performed by heating a mixture of the heterocyclic salt and an alkali metal or alkaline earth metal hydroxide such as sodium hydroxide or potassium hydroxide in the presence of air to a temperature in the range for example 20° to 300° C., preferably in the range 20° to 50° C.

The oxidation is preferably performed in the presence of an aqueous solution of a suitable base such as an aqueous solution of an alkali metal or alkaline earth metal hydroxide, for example, sodium hydroxide or potassium hydroxide, and using a mild oxidant such as an aqueous solution of an alkali metal or alkaline earth metal Fe(III) salt such as sodium or potassium ferricyanide. Alternative mild oxidants under such basic conditions include, for example, peroxides such as hydrogen peroxide and, for example, alkali metal or alkaline earth metal permanganates such as potassium permanganate. The reaction is conveniently performed in the presence of a suitable inert co-solvent or diluent such as toluene, 1,2-dimethoxyethane, tetrahydrofuran or 1,4-dioxan and at a temperature in the range, for example 0° to 100° C., conveniently in the range 20° to 70° C.

Conveniently this process variant is utilised for the production of those compounds of the formula I wherein $Ar^1$ is a (1-4C)alkyl-2-oxo-1,2-dihydroquinolinyl moiety by the reaction of a compound of the formula I wherein $Ar^1$ is a quinolyl moiety with a (1-4C)alkyl chloride, bromide or iodide and the oxidation of the quinolinium salt so obtained.

As stated previously conventional protecting groups are utilised, where appropriate, within the process variants described hereinbefore. Examples of such protecting groups are provided below:

A suitable protecting group for an amino or alkylamino group is, for example, an acyl group for example a (1-4C)alkanoyl group (especially acetyl), a (1-4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (1-4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formulae II, III and IV described within process variants (a) to (d) above may be obtained by standard procedures of organic chemistry. The preparation of examples of some of these starting materials is described within the accompanying non-limiting Examples which are provided for the purpose of illustration only. The appropriate unsubstituted heterocyclic moiety required as a starting material for process variant (h) above may be obtained by one or more of process variants (a) to (d) above. The preparation, for example, of an appropriate quinolyl moiety is described within the accompanying non-limiting Examples which are provided for the purpose of illustration only. Other necessary starting materials are obtainable by analogous procedures to those described or by modifications thereto which are within the ordinary skill of an organic chemist.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae II, III and IV and these are provided as a further feature of the invention.

As stated previously, the benzodioxole derivatives of the formula I are inhibitors of the enzyme 5-LO. The effects of this inhibition may be demonstrated using one or more of the standard procedures set out below:

a) An in vitro assay system involving incubating a test compound with heparinised human blood, prior to challenge with the calcium ionophore A23187 and the indirectly measuring the inhibitory effects on 5-LO by assaying the amount of $LTB_4$ using specific radioimmunoassays described by Carey and Forder (F. Carey and R.A. Forder, *Prostaglandins Leukotrienes Med.*, 1986, 22, 57; *Prostaglandins*, 1984, 28, 666; *Brit. J. Pharmacol.* 1985, 84, 34P) which involve the use of a protein-$LTB_4$ conjugate produced using the procedure of Young et alia (*Prostaglandins*, 1983, 26(4), 605–613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(T \times B_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

b) An ex vivo assay system, which is a variation of test a) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

c) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–c):

| Test a): | $IC_{50}$ ($LTB_4$) in the range, for example, 0.05–40 $\mu M$ |
| --- | --- |
| | $IC_{50}$ ($TxB_2$) in the range, for example, 40–200 $\mu M$; |
| Test b): | oral $ED_{50}$ ($LTB_4$) in the range, for example, 0.1–100 mg/kg; |
| Test c): | oral $ED_{50}$ ($LTB_4$) in the range for example, 0.1–50 mg/kg. |

No overt toxicity or other untoward effects are present in tests b) and/or c) when compounds of the formula I are administered at several multiples of their minimum inhibitory dose or concentration.

Thus, by way of example, the compound 5-(4-methoxytetrahydropyran-4-yl)-2-(1-methyl-2-oxo-1,2-dihydroquinolin-6-yl)benzo-1,3-dioxole has an $IC_{50}$ of 0.38$\mu M$ against $LTB_4$ in test a) and an oral $ED_{50}$ of <0.5 mg/kg versus $LTB_4$ in test c). In general those compounds of the formula I which are particularly preferred have an $IC_{50}$ of <1 $\mu M$ against $LTB_4$ in test a), and an oral $ED_{50}$ of <100 mg/kg against $LTB_4$ in tests b) and c).

These compounds are examples of benzodioxole derivatives of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a benzodioxole derivative of the formula I as defined hereinbefore, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension.

In general the above compositions may be prepared in a conventional manner using conventional excipients.

The amount of active ingredient (that is a benzodioxole derivative of the formula I as defined hereinbefore, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a benzodioxole derivative of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a benzodioxole derivative of the formula I will naturally vary according to the nature and severity of the conditions, the age and sex of the animal or patient and the route of administration, according to well known principles of medicine. As mentioned above, benzodioxole derivatives of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory nonsteroidal anti-inflammatory agents (NSAIA), such as indomethacin, acetylsalicylic acid, ibuprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a benzodioxole derivative of the formula I as defined hereinbefore, or a pharmaceutically-acceptable salt thereof, in conjunction or admixture with a cyclooxygenase inhibitory nonsteroidal anti-inflammatory agent (such as those mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after recrystallisation from a conventional organic solvent such as ethanol, methanol, acetone, ether or hexane, alone or in admixture; and (viii) the following abbreviations have been used:

| THF | tetrahydrofuran; |
| DMF | N,N-dimethylformamide. |

EXAMPLE 1

A solution of sodium metaperiodate (1.6 g) in water (19 ml) was added to a solution of 2-hydroxy-5-(4-methoxytetrahydropyran-4-yl)-α-(6-quinolyl)benzyl alcohol (2.13 g) in methanol (112 ml) and the mixture was stirred at ambient temperature for 24 hours. The mixture was filtered and the methanol was evaporated. The residue was partitioned between ethyl acetate and water. The organic phase was washed with water, dried (MgSO$_4$) and evaporated. The residue was purified by column chromatography using increasingly polar mixtures of ethyl acetate and hexane as eluent. There was thus obtained 5-(4-methoxytetrahydropyran-4-yl)-2-(6-quinolyl)benzo-1,3-dioxole (0.588 g, 28%), m.p. 133°–135° C.

The 2-hydroxy-5-(4-methoxytetrahydropyran-4-yl)-α-(6-quinolyl)benzyl alcohol used as a starting material was obtained as follows:

A mixture of 5-bromo-2-hydroxybenzyl alcohol (1.42 g), tert-butyldimethylsilyl chloride (2.54 g), imidazole (2.38 g) and DMF (5 ml) was stirred at ambient temperature for 16 hours. The mixture was poured into aqueous sodium bicarbonate solution (5% w/v, 40 ml) and extracted with ethyl acetate. The organic phase was washed with brine, dried (MgSO$_4$) and evaporated. There was thus obtained tert-butyldimethylsilyl 5-bromo-2-tert-butyldimethylsilyloxybenzyl ether (3.1 g) as a colourless liquid which was used without further purification.

n-Butyl-lithium (1.6M in hexane, 2.75 ml) was added dropwise to a solution of a portion (1.724 g) of the product so obtained in THF (32 ml) which has been cooled to −78° C. The mixture was stirred at −78° C. for 15 minutes. A solution of tetrahydropyran-4-one (0.5 ml) in THF (1 ml) was added and the mixture was stirred at −78° C. for 30 minutes. The mixture was allowed to warm to −20° C. A saturated aqueous ammonium chloride solution (30 ml) was added and the mixture was extracted with ethyl acetate. The organic phase was washed with brine, dried (MgSO$_4$) and evaporated. The residue was purified by column chromatography using increasingly polar mixtures of hexane and ethyl acetate as eluent. There was thus obtained 4-[4-tert-butyldimethylsilyloxy-3-(tert-butyldimethylsilyloxymethyl)phenyl]-4-hydroxytetrahydropyran (0.984 g, 54%), m.p. 67°–69° C.

After repetition of the above-described steps, a mixture of the product so obtained (3.6 g), sodium hydride (60% w/w dispersion in mineral oil, 0.518 g) and THF (60 ml) was stirred at 0° C. for 30 minutes. Methyl iodide (4 ml) was added and the mixture was stirred at ambient temperature for 16 hours. The mixture was partitioned between ethyl acetate and a saturated aqueous ammonium chloride solution. The organic phase was washed with brine, dried (MgSO$_4$) and evaporated.

The residue was purified by column chromatography using increasingly polar mixtures of hexane and ethyl acetate as eluent. There was thus obtained 4-[4-tert-butyldimethylsilyloxy-3-(tert-butyldimethylsilyloxymethyl)phenyl]-4-methoxytetrahydropyran (1.98 g, 54%), m.p. 51°–53° C.

Tetra-n-butylammonium fluoride (1M in THF, 3 ml) was added to a solution of a portion (0.39 g) of the product so obtained in THF (10 ml) and the mixture was stirred at ambient temperature for 1.5 hours. The mixture was partitioned between ethyl acetate and a saturated aqueous ammonium chloride solution. The organic phase was washed with brine, dried (MgSO4) and evaporated. The residue was purified by column chromatography using increasingly polar mixtures of hexane and ethyl acetate as eluent. There was thus obtained 2-hydroxy-5-(4-methoxytetrahydropyran-4-yl)benzyl alcohol (0.172 g, 84%), m.p. 120°–121° C.

After appropriate repetition of the above-described steps, a solution of Jones Reagent (8N chromic acid, 2 ml) in acetone (20 ml) was added dropwise to a solution of the product so obtained (0.805 g) in acetone (30 ml) which had been cooled to 0° C. The mixture was stirred at 0° C. for 20 minutes. Isopropanol (5 drops) was added and the mixture was filtered. The filtrate was evaporated and the residue was partitioned between diethyl ether and water. The organic phase was washed with a saturated aqueous sodium bicarbonate solution, with water and brine, dried (MgSO4) and evaporated. The residue was purified by column chromatography using increasingly polar mixtures of hexane and ethyl acetate as eluent. There was thus obtained 5-(4-methoxytetrahydropyran-4-yl)salicylaldehyde (0.327 g, 41%), m.p. 74°–75° C.

A solution of 6-bromoquinoline (0.512 g) in THF (1 ml) was added dropwise to a mixture of n-butyl-lithium (1.6M in hexane, 2 ml), hexane (1 ml) and THF (1 ml) which had been cooled to −100° C. The mixture was stirred at −100° C. for 2 minutes. A solution of 5-(4-methoxytetrahydropyran-4-yl)salicylaldehyde (0.29 g) in THF (1 ml) was added and the mixture was allowed to warm to −20° C. A saturated aqueous ammonium chloride solution was added and the mixture was extracted with ethyl acetate. The organic phase was washed with water and with brine, dried (MgSO4) and evaporated. The residue was purified by column chromatography using increasingly polar mixtures of hexane and ethyl acetate as eluent. There was thus obtained 2-hydroxy-5-(4-methoxytetrahydropyran-4-yl)-α-(6-quinolyl)benzyl alcohol (0.165 g, 37%), m.p. 80°–85° C.

EXAMPLE 2

Methyl iodide (1.5 ml) was added to a solution of 5-(4-methoxytetrahydropyran-4-yl)-2-(6-quinolyl)benzo-1,3-dioxole (0.54 g) in acetonitrile (10 ml) and the mixture was stirred at ambient temperature for 72 hours. Diethyl ether (30 ml) was added and the precipitate was isolated. There was thus obtained 6-[5-(4-methoxytetrahydropyran-4-yl)benzo-1,3-dioxol-2-yl]-1-methylquinolinium iodide (0.648 g, 86%), m.p. 169° C. (decomposes).

To a solution of a portion (0.5 g) of the quinolinium iodide so obtained in 1,4-dioxan (4.3 ml) was added a solution of potassium ferricyanide (1.5 g) in aqueous sodium hydroxide solution (10% w/v, 4.3 ml). The mixture was stirred at ambient temperature for 2.5 hours. The mixture was partitioned between diethyl ether and water. The organic phase was washed with water and with brine, dried (MgSO4) and evaporated. The residue was purified by column chromatography using increasingly polar mixtures of hexane and ethyl acetate as eluent. There was thus obtained 5-(4-methoxytetrahydropyran-4-yl)-2-(1-methyl-2-oxo-1,2-dihydroquinolin-6-yl)benzo-1,3-dioxole (0.345 g, 89%), m.p. 63°–65° C.

CHEMICAL FORMULAE

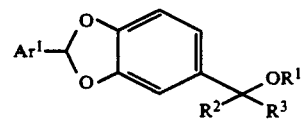

I

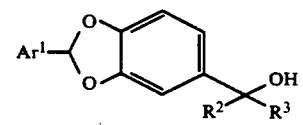

II

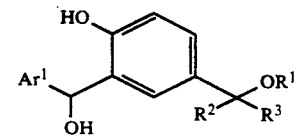

III

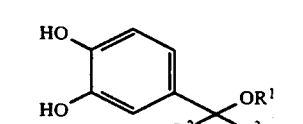

IV

We claim:
1. A benzodioxole derivative of the formula I

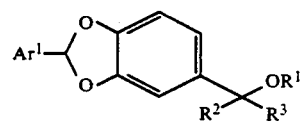

I where $Ar^1$ is a 9- or 10-membered bicyclic heterocyclic moiety containing one or two nitrogen heteroatoms or containing a further heteroatom selected from nitrogen, oxygen and sulphur, and $Ar^1$ is unsubstituted or is further substituted by up to three substituents selected from amino, halogeno, hydroxy, cyano, oxo, thioxo, (1–4C)alkyl, (1–4C)alkoxy, (1–4C)alkylthio, (1–4C)alkylsulphinyl, (1–4C)alkylsulphonyl, (1–4C)alkylamino, di-[(1–4C)alkyl]amino, (1–4C)alkoxycarbonyl, (2–4C)alkanoyl and fluoro-(1–4C)alkyl;

wherein the benzodioxole ring is unsubstituted or is substituted by one or two substituents selected from halogeno, hydroxy, (1–4C)alkyl, (1–4C)alkoxy and fluoro-(1–4C)alkyl;

wherein $R^1$ is (1–6C)alkyl, (3–6C)alkenyl or (3–6C)alkynyl; and wherein $R^2$ and $R^3$ together for a group of the formula —$A^1$—X—$A^2$— which, together with the carbon atom to which $A^1$ and $A^2$ are attached, defines a ring having 5 to 7 ring atoms, wherein $A^1$ and $A^2$, which are the same or different, each is (1–3C)alkylene and X is oxy, thio, sulphinyl or sulphonyl, and which ring is unsubstituted or unsubstituted by one or two substituents, which are the same or different, selected from hydroxy, (1–4

C)alkyl and (1–4C)alkoxy; or a pharmaceutically-acceptable salt thereof.

2. A benzodioxole derivative of the formula I as claimed in claim 1 wherein $Ar^1$ is 1-methyl-2-oxo-1,2-dihydroquinolin-6-yl, 1-ethyl-2-oxo-1,2-dihydroquinolin-6-yl, 1-methyl-2-oxo-1,2,3,4-tetrahydroquinolin-6-yl, 1-ethyl-2-oxo-1,2,3,4-tetrahydroquinolin-6-yl or the corresponding 2-thioxo derivatives, or $Ar^1$ is 4-methyl-3-oxo-2,3-dihydro-4H-1,4-benzoxazin-7-yl; the benzodioxole ring bears no additional substituents; $R^1$ is methyl, ethyl or allyl; and $R^2$ an $R^3$ together from a group of the formula $-A^1-X-A^2-$ which, together with the carbon atom to which $A^1$ and $A^2$ are attached, defines a ring having 5 or 6 ring atoms, wherein $A^1$ is ethylene, $A^2$ is methylene or ethylene and X is oxy, and which ring is unsubstituted or substituted by a substituent selected from methyl and ethyl; or a pharmaceutically-acceptable salt thereof.

3. A benzodioxole derivative of the formula I as claimed in claim 1 wherein $Ar^1$ is 1-methyl-2-oxo-1,2-dihydroquinolin-6-yl, 1-methyl-2-thioxo-1,2-dihydroquinolin-6-yl, 1-methyl-2-oxo-1,2,3,4-tetrahydroquinolin-6-yl, 1-methyl-2-thioxo-1,2,3,4-tetrahydroquinolin-6-yl or 4-methyl-3-oxo-2,3-dihydro-4H-1,4-benzoxazin-7-yl; the benzodioxole ring bears no additional substituents; $R^1$ is methyl; and $R^2$ and $R^3$ together form a group of the formula $-A^1-X-A^2-$ which, together with the carbon atom to which $A^1$ and $A^2$ are attached, defines a ring having 6 ring atoms, wherein $A^1$ is ethylene, $A^2$ is ethylene and X is oxy, and which ring is unsubstituted or substituted by a methyl substituent alpha to X; or a pharmaceutically-acceptable salt thereof.

4. A benzodioxole derivative of the formula I, or a pharmaceutically-acceptable salt thereof, as claimed in claim 1 being:
5-(4-methoxytetrahydropyran-4-yl)-2-(1-methyl-2-oxo-1,2-dihydroquinolin-6-yl)benzo-1,3-dioxole.

5. A pharmaceutical composition which comprises a benzodioxole derivative of the formula I, or a pharmaceutically-acceptable salt thereof, as claimed in any one of claims 2 to 4 and 1 in association with a pharmaceutically-acceptable diluent or carrier.

6. A pharmaceutical composition which comprises a benzodioxole derivative of the formula I, or a pharmaceutically-acceptable salt thereof, as claimed in any one of claims 2 to 4 and 1 in conjunction or admixture with a cyclooxygenase inhibitory non-steroidal anti-inflammatory agent, and a pharmaceutically-acceptable diluent or carrier.

7. A method of treating a disease or medical condition mediated alone or in part by one or more leukotrienes which comprises administering to a warm-blooded animal requiring such treatment an effective amount of a benzodioxole derivative of the formula I, or a pharmaceutically-acceptable salt thereof, as claimed in any one of claims 2 to 4 and 1.

* * * * *